United States Patent [19]
Metzger et al.

[11] Patent Number: 6,143,889
[45] Date of Patent: *Nov. 7, 2000

[54] ASYMMETRIC STILBENE COMPOUNDS

[75] Inventors: Georges Metzger, Moernach, France; Dieter Reinehr, Kandern, Germany; Claude Eckhardt, Riedisheim; Fabienne Cuesta, Roppentzwiller, both of France

[73] Assignee: Ciba Specialty Chemicals Corporation, Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/209,940

[22] Filed: Dec. 11, 1998

[30] Foreign Application Priority Data

Dec. 13, 1997 [GB] United Kingdom .................. 97 26365

[51] Int. Cl.$^7$ .................................................. C07D 251/08
[52] U.S. Cl. ........................................ 544/193.2; 510/495
[58] Field of Search ......................... 544/193.2; 510/492, 510/276, 301, 495; 252/8.63; 8/566, 190

[56] References Cited

U.S. PATENT DOCUMENTS

| | | | |
|---|---|---|---|
| 3,177,207 | 4/1965 | Siegel et al. | 544/193.2 |
| 3,351,592 | 11/1967 | Siegrist et al. | 544/193.2 |
| 4,587,195 | 5/1986 | Ishikawa et al. | 544/193.2 |
| 4,900,651 | 2/1990 | Ishikawa et al. | 430/380 |
| 5,744,599 | 4/1998 | Reinehr et al. | 544/193.2 |
| 5,892,031 | 4/1999 | Reinhr et al. | 544/193.2 |
| 5,939,379 | 8/1999 | Echhardt et al. | 544/193.2 |

FOREIGN PATENT DOCUMENTS

| | | |
|---|---|---|
| 0728749 | 8/1996 | European Pat. Off. . |
| 0808837 | 11/1997 | European Pat. Off. . |
| 0850934 | 7/1998 | European Pat. Off. . |
| 1211812 | 11/1970 | United Kingdom . |
| 1218160 | 1/1971 | United Kingdom . |
| 1240020 | 7/1971 | United Kingdom . |
| 1318217 | 5/1973 | United Kingdom . |
| 1384458 | 2/1975 | United Kingdom . |
| 2171407 | 8/1986 | United Kingdom . |
| 94/04515 | 3/1994 | WIPO . |
| 97/46541 | 12/1997 | WIPO . |
| 98/42685 | 10/1998 | WIPO . |

OTHER PUBLICATIONS

Chem. Abstr. 125:250256v (1996), Eckhardt et al, Chemical Abstracts, vol. 125, No. 20, p. 140 (no month available).

*Primary Examiner*—Caroline D. Liott
*Attorney, Agent, or Firm*—Kevin T. Mansfield

[57] ABSTRACT

Asymmetric compounds having the formula:

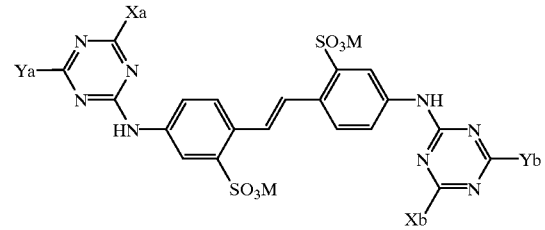

(1)

in which M is hydrogen, an alkali metal atom, ammonium or a cation formed from an amine: Xa and Xb are the same or different and each is $NH_2$; $NH(C_1-C_4 alkyl)$; $NH(C_{2-4}alkoxyalkyl)$; $N(C_1-C_4 alkyl)_2$; $N(CH_2CH_2OH)_2$; a group $NH-Z-NR_1R_2$ in which Z is $C_2-C_{14}$alkylene or optionally substituted arylene, and $R_1$ and $R_2$ are the same or different and each is $C_1-C_{12}$alkyl or $R_1$ and $R_2$, together with the nitrogen atom to which they are each attached, form a morpholino, piperidino or piperazino ring; an aminoacid residue; $C_1-C_4$alkoxy; hydroxy-substituted-$C_2-C_4$alkoxy;

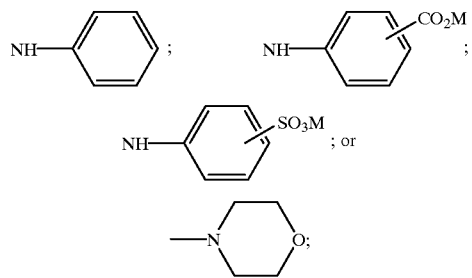

and Ya and Yb are the same or different and each is a substituted amino group having both UVA and UVB-absorbing properties having the formula:

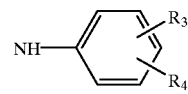

(2)

in which $R_3$ is CN; $SO_2R_5$ in which $R_5$ is $C_1-C_{12}$alkyl, $C_1-C_{12}$alkoxy, $NH_2$, $NH(C_1-C_4 alkyl)$, $N(C_1-C_4 alkyl)_2$, $N(CH_2CH_2OH)_2$, $C_1-C_4$alkoxy or hydroxy-substituted-$C_2-C_4$alkoxy; $COR_5$. In which $R_5$ has its previous significance; COOM or $NHCOR_5$ and in which $R_4$ has the same meaning as $R_3$ or H, OH, $C_1-C_4$alkyl or $C_1-C_4$alkoxy and one of Xa and Xb can be identical to one of Ya and Yb, provided that one of Xa and Xb is different from the other and/or one of Ya and Yb is different from the other, and their use improve the sun protection factor (SPF) of textile fiber material.

13 Claims, No Drawings

ASYMMETRIC STILBENE COMPOUNDS

The present invention relates to new compounds, in particular to new asymmetric stilbene UV absorber compounds which are useful as sun protection agents; and to a method of improving the sun protection factor (SPF) of textile fibre material, especially cotton, polyamide and wool, comprising treating them with the new compounds.

It is known that light radiation of wavelengths 280–400 nm permits tanning of the epidermis. Also known is that rays of wavelengths 280–320 nm (termed UV-B radiation), cause erythemas and skin burning which can inhibit skin tanning.

Radiation of wavelengths 320–400 nm (termed UV-A radiation) is known to induce skin tanning but can also cause skin damage, especially to sensitive skin which is exposed to sunlight for long periods. Examples of such damage include loss of skin elasticity and the appearance of wrinkles, promotion of the onset of erythemal reaction and the inducement of phototoxic or photoallergic reactions.

Any effective protection of the skin from the damaging effects of undue exposure to sunlight clearly needs to include means for absorbing both UV-A and UV-B components of sunlight before they reach the skin surface.

Traditionally, protection of exposed human skin against potential damage by the UV components in sunlight has been effected by directly applying to the skin a preparation containing a UV absorber. In areas of the world, e.g. Australia and America, which enjoy especially sunny climates, there has been a great increase in the awareness of the potential hazards of undue exposure to sunlight, compounded by fears of the consequences of alleged damage to the ozone layer. Some of the more distressing embodiments of skin damage caused by excessive, unprotected exposure to sunlight are development of melanomas or carcinomas on the skin.

One aspect of the desire to increase the level of skin protection against sunlight has been the consideration of additional measures, over and above the direct protection of the skin. For example, consideration has been given to the provision of protection to skin covered by clothing and thus not directly exposed to sunlight.

Most natural and synthetic textile materials are at least partially permeable to UV components of sunlight. Accordingly, the mere wearing of clothing does not necessarily provide skin beneath the clothing with adequate protection against damage by UV radiation. Although clothing containing a deeply coloured dye and/or having a tight weave texture may provide a reasonable level of protection to skin beneath it, such clothing is not practical in hot sunny climates, from the standpoint of the personal comfort of the wearer.

There is a need, therefore, to provide protection against UV radiation for skin which lies underneath clothing, including lightweight summer clothing, which is undyed or dyed only in pale shades. Depending on the nature of the dyestuff, even skin beneath clothing dyed in some dark shades may also require protection from UV radiation.

Such lightweight summer clothing normally has a density of less than 200 g/m² and has a sun protection factor rating between 1.5 and 20, depending on the type of fibre from which the clothing is manufactured.

The SPF rating of a sun protectant (sun cream or clothing) may be defined as the multiple of the time taken for the average person wearing the sun protectant to suffer sun burning under average exposure to sun. For example, if an average person would normally suffer sun burn after 30 minutes under standard exposure conditions, a sun protectant having an SPF rating of 5 would extend the period of protection from 30 minutes to 2 hours and 30 minutes. For people living in especially sunny climates, where mean sun burn times are minimal, e.g. only 15 minutes for an average fair-skinned person at the hottest time of the day, SPF ratings of at least 20 are desired for lightweight clothing.

It is already known, e.g. from WO 94/4515, that the application of specified types of UVA to a light-weight textile materials in general can effect an increase in the SPF value of the textile so treated. The increase in SPF value achieved thereby, however, is relatively modest.

The use of fluorescent whitening agents (FWAs) in order to effect an increase in the SPF value of textiles has also been proposed. Most FWAs, however, are only effective in absorbing radiation in the UV-A range. Certain symmetric FWAs have been disclosed in EP-A-728,749 which absorb radiation in both the UV-A and UV-B ranges, and impart greatly increased SPF ratings to textile fibre materials treated with them.

In Chem.Abstracts, 1962, 12913a (Japan 14,728), there are described certain asymmetric FWAs, but these known compounds have no UV-B absorbing properties so that they are not able to impart useful SPF ratings to textile materials treated with them.

Certain new asymmetric stilbene UV absorber compounds have now been found which, relative to known symmetric stilbene UV absorber compounds, are easy to formulate and impart both excellent whiteness levels and SPF ratings to textile materials treated with them.

Accordingly, the present invention provides, as a first aspect, an asymmetric compound having the formula:

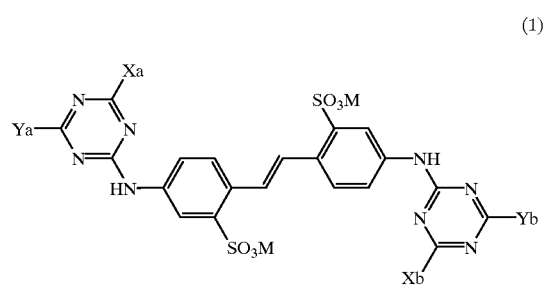

(1)

in which M is hydrogen, an alkali metal atom, ammonium or a cation formed from an amine; Xa and Xb are the same or different and each is $NH_2$; $NH(C_1-C_4 alkyl)$; $N(C_1-C_4 alkyl)_2$; $NH(C_2-C_4 alkoxyalkyl)$; $N(CH_2CH_2OH)_2$; a group $NH-Z-NR_1R_2$ in which Z is $C_2-C_4$ alkylene or optionally substituted arylene, and $R_1$ and $R_2$ are the same or different and each is $C_1-C_{12}$ alkyl or $R_1$ and $R_2$, together with the nitrogen atom to which they are each attached, form a morpholino, piperidino or piperazino ring; an aminoacid residue; $C_1-C_4$ alkoxy; hydroxy-substituted-$C_2-C_4$ alkoxy;

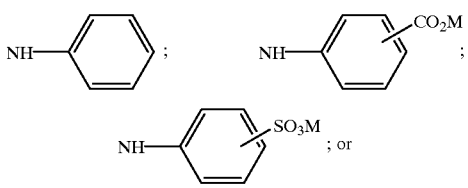

Ya and Yb are the same or different and each is a substituted amino group having both UVA and UVB-absorbing properties, preferably a group having the formula:

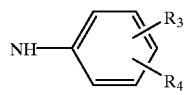

(2)

in which $R_3$ is CN; $SO_2R_5$ which $R_5$ is, $C_1$–$C_{12}$alkyl, $C_1$–$C_{12}$alkoxy, $NH_2$, $NH(C_1$–$C_4$alkyl), $N(C_1$–$C_4$alkyl)$_2$, $N(CH_2CH_2OH)_2$, $C_1$–$C_4$alkoxy or hydroxy-substituted-$C_2$–$C_4$alkoxy; $COR_5$ in which $R_5$ has its previous significance; COOM in which M has its previous significance or $NHCOR_5$ in which $R_5$ has its previous significance and $R_4$ has the same significance as $R_3$ or is H, OH, $C_1$–$C_4$alkyl or $C_1$–$C_4$alkoxy; and one of Xa and Xb can be identical to one of Ya and Yb, provided that one of Xa and Xb is different from the other and/or one of Ya and Yb is different from the other.

Preferably, M is hydrogen, sodium, potassium, calcium, magnesium, ammonium, mono-, di-, tri- or tetra-$C_1$–$C_4$alkylammonium, mono-, di-, tri- or tetra-$C_1$–$C_4$hydroxyalkylammonium, or ammonium that is di- or tri-substituted with a mixture of $C_1$–$C_4$alkyl and $C_1$–$C_4$hydroxyalkyl groups. Preferably, each M is sodium.

When one or more of Xa, Xb and $R_5$ are $NH(C_1$–$C_4$alkyl), examples of such groups are NH-ethyl, NH-n-propyl, NH-isopropyl, NH-n-butyl and, in particular, NH-methyl groups.

When one or more of Xa, and Xb are $NH(C_2$–$C_4$alkoxyalkyl), examples of such groups are ethoxyethyl, methoxypropyl and, in particular, methoxyethyl.

When one or more of Xa, Xb and $R_5$ are $N(C_1$–$C_4$alkyl)$_2$, examples of such groups are N(ethyl)$_2$, N(n-propyl)$_2$, N(isopropyl)$_2$, N(n-butyl)$_2$ and, in particular, N(methyl)$_2$ groups.

When one or both of Xa and Xb is a group NH—Z—$NR_1R_2$, $C_2$–$C_4$alkylene groups Z include, e.g., ethylene, 1,3-propylene, 1,4-butylene, 1,5-pentylene, 1,6-hexylene, 1,8-octylene, 1,10-decylene, 1,12-dodecylene and 1,14-tetradecylene groups. Preferred are $C_2$–$C_6$alkylene groups Z, most preferably the 1,3-propylene group. Optionally substituted arylene Z include the naphthylene and, preferably, the phenylene group. The optionally substituted arylene Z may be substituted, for example with one or more $C_1$–$C_4$alkyl groups. $C_1$–$C_{12}$alkyl groups $R_1$ and $R_2$ may be, e.g., methyl, ethyl, n-propyl, isopropyl, n-butyl, n-pentyl, n-hexyl, n-octyl, n-decyl and n-dodecyl groups, preferably methyl or ethyl groups.

An aminoacid residue Xa and/or Xb may be, e.g., one having the formula —NH—CH(CO$_2$H)R$_6$ in which $R_6$ is hydrogen or a group having the formula —CHR$_7$R$_8$ in which $R_7$ and $R_8$, independently, are hydrogen or $C_1$–$C_4$alkyl optionally substituted by one or two substituents selected from hydroxy, thio, methylthio, amino, carboxy, sulfo, phenyl, 4-hydroxyphenyl, 3,5-diiodo-4-hydroxyphenyl, β-indolyl, β-imidazolyl and NH=C(NH$_2$)NH—.

Specific examples of aminoacids from which such preferred aminoacid residues Xa and/or Xb are derived include glycine, alanine, sarcosine, serine, cysteine, phenylalanine, tyrosine (4-hydroxyphenylalanine), diiodotyrosine, tryptophan (β-indolylalanine), histidine ((β-imidazolylalanine), α-aminobutyric acid, methionine, valine (α-aminoisovaleric acid), norvaline, leucine (α-aminoisocaproic acid), isoleucine (α-amino-β-methylvaleric acid), norleucine (α-amino-n-caproic acid), arginine, ornithine (α,δ-diaminovaleric acid), lysine (α,ε-diaminocaproic acid), aspartic acid (aminosuccinic acid), glutamic acid (α-aminoglutaric acid), threonine, hydroxyglutamic acid and taurine, as well as mixtures and optical isomers thereof. Of these aminoacids from which such preferred aminoacid residues Xa and/or Xb are derived, sarcosine, taurine, glutamic acid and aspartic acid are particularly preferred.

A further preferred example of an aminoacid from which an aminoacid residue Xa and/or Xb may be derived is iminodiacetic acid.

Other, less preferred examples of aminoacids from which aminoacid residues Xa and/or Xb may be derived include cystine, lanthionine, proline and hydroxyproline.

A $C_1$–$C_4$alkoxy residue Xa and/or Xb, $R_4$ or $R_5$ may be, e.g., ethoxy, n-propoxy, isopropoxy, n-butoxy or, especially, methoxy residue.

An hydroxy-substituted-$C_2$–$C_4$alkoxy group Xa and/or Xb or $R_5$ may be, e.g., 2-hydroxyethoxy, 3-hydroxypropoxy or 4-hydroxybutoxy group.

A $C_1$–$C_4$alkyl group $R_4$ may be, e.g., ethyl, n-propyl, isopropyl, n-butyl or, especially, methyl group.

Preferred asymmetric compounds of formula (1) are those in which Xa and Xb are the same and Ya and Yb are different; and those in which Ya and Yb are the same and Xa and Xb are different.

In the groups Ya and Yb of formula (2), preferably the substituents $R_3$ and $R_4$ are in the 2 and 4-positions relative to the NH substituent.

Preferably, in the groups Ya and Yb of formnula (2), $R_3$ is CN; $SO_2R_5$ in which $R_5$ is , $C_1$–$C_{12}$alkyl, $C_1$14$C_{12}$alkoxy, $NH_2$, $NH(C_1$–$C_4$alkyl), $N(C_1$–$C_4$alkyl)$_2$, $N(CH_2CH_2OH)_2$, $C_1$–$C_4$alkoxy or hydroxy-substituted-$C_2$–$C_4$alkoxy; $COR_5$ in which $R_5$ has its previous significance; COOM in which M has its previous significance or $NHCOR_5$ in which $R_5$ has its previous significance and in $R_4$ is hydrogen.

The asymmetric compounds of formula (1) may be produced by reacting, under known reaction conditions, cyanuric chloride, successively, in any desired sequence, with each of an aminostilbene-sulfonic acid, an amino compound capable of introducing a group Xa and Xb in which Xa and Xb have their previous significance, and a compound capable of introducing a group Ya and Yb in which Ya and Yb have their previous significance, provided that one of Xa and Xb is different from the other and/or one of Ya and Yb is different from the other. Alternatively, the asymmetric compounds of formula (1) can be obtained as a mixture with the analogous symmetric compounds by reacting, in one pot, cyanuric chloride, an aminostilbene-sulfonic acid, and the respective stoichiometric amounts of an amino compound capable of introducing a group Xa and Xb, in which Xa and Xb have their previous significance, and a compound capable of introducing a group Ya and Yb, in which Ya and Yb have their previous significance.

The starting materials are known compounds which are readily available.

Especially preferred asymmetric compounds of formula (1) are those obtained in the form of a mixture with the analogous symmetric compounds by reacting, in one pot, the respective stoichiometric amounts of cyanuric chloride, each of an aminostilbene-sulfonic acid, an amino compound capable of introducing a group Xa and Xb, in which Xa and Xb have their previous significance, and a compound capable of introducing a group Ya and Yb, in which Ya and Yb have their previous significance. For example, if Ya and Yb are the same and Xa and Xb are different, in this way, there is obtained a mixture of the following compounds:

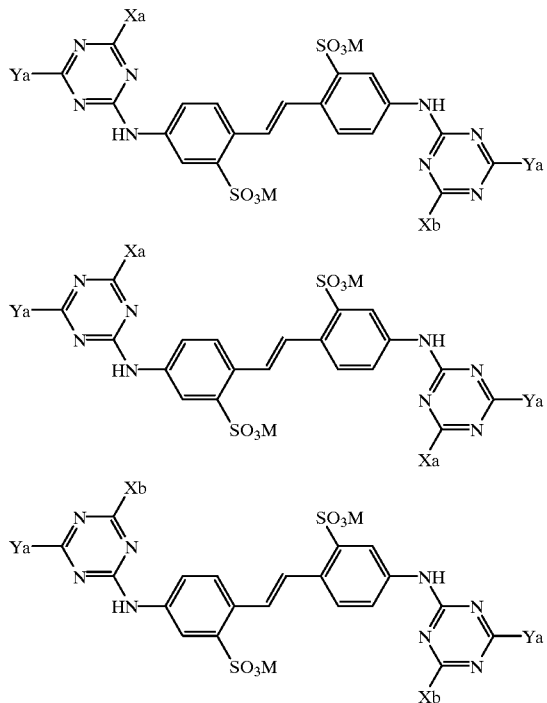

The present invention also provides, as a second aspect, a method for the improvement of the SPF of a textile fibre material, comprising treating the textile fibre material with 0.05 to 3.0% by weight, based on the weight of the textile fibre material, of one or more compounds having the formula (1).

The textile fibres treated according to the method of the present invention may be natural or synthetic fibres or mixtures thereof. Examples of natural fibres include vegetable fibres such as cotton, viscose, flax, rayon or linen, preferably cotton and animal fibres such as wool, mohair, cashmere, angora and silk, preferably wool. Synthetic fibres include polyester, polyamide and polyacrylonitrile fibres. Preferred textile fibres are cotton, polyamide and wool fibres.

Preferably, textile fibres treated according to the method of the present invention have a density of less than 200 g/m$^2$ and have not been previously dyed in deep shades.

Some of the compounds of formula (1) used in the method of the present invention may be only sparingly soluble in water and may need to be applied in dispersed form. For this purpose, they may be milled with an appropriate dispersant, conveniently using quartz balls and an impeller, down to a particle size of 1–2 microns.

As dispersing agents for such sparingly-soluble compounds of formula (1) there may be mentioned:

acid esters or their salts of alkylene oxide adducts, e.g., acid esters or their salts of a polyadduct of 4 to 40 moles of ethylene oxide with 1 mole of a phenol, or phosphoric acid esters of the adduct of 6 to 30 moles of ethylene oxide with 1 mole of 4-nonylphenol, 1 mole of dinonylphenol or, especially, with 1 mole of compounds which have been produced by the addition of 1 to 3 moles of styrenes on to 1 mole of phenol;

polystyrene sulphonates;

fatty acid taurides;

alkylated diphenyloxide-mono- or -di-sulphonates;

sulphonates of polycarboxylic acid esters;

addition products of 1 to 60, preferably 2 to 30 moles of ethylene oxide and/or propylene oxide on to fatty amines, fatty amides, fatty acids or fatty alcohols, each having 8 to 22 carbon atoms, or on to tri- to hexavalent $C_3$–$C_6$ alkanols, the addition products having been converted into an acid ester with an organic dicarboxylic acid or with an inorganic polybasic acid;

lignin sulphonates; and, in particular formaldehyde condensation products, e.g., condensation products of lignin sulphonates and/or phenol and formaldehyde; condensation products of formaldehyde with aromatic sulphonic acids, e.g., condensation products of ditolylethersulphonates and formaldehyde; condensation products of naphthalenesulphonic acid and/or naphthol- or naphthylaminesulphonic acids and formaldehyde; condensation products of phenolsulphonic acids and/or sulphonated dihydroxydiphenylsulphone and phenols or cresols with formaldehyde and/or urea; or condensation products of diphenyloxide-disulphonic acid derivatives with formaldehyde.

Depending on the type of compound of formula (1) used, it may be beneficial to carry out the treatment in a neutral, alkaline or acidic bath. The method is usually conducted in the temperature range of from 20 to 140° C., for example at or near to the boiling point of the aqueous bath, e.g. at about 90° C.

Solutions of the compound of formula (1), or its emulsions in organic solvents may also be used in the method of the present invention. For example, the so-called solvent dyeing (pad thermofix application) or exhaust dyeing methods in dyeing machines may be used.

If the method of the present invention is combined with a textile treatment or finishing method, such combined treatment may be advantageously carried out using appropriate stable preparations which contain the compound of formula (1) in a concentration such that the desired SPF improvement is achieved.

In certain cases, the compound of formula (1) is made fully effective by an after-treatment. This may comprise a chemical treatment such as treatment with an acid, a thermal treatment or a combined thermal/chemical treatment.

It is often advantageous to use the compound of formula (1) in admixture with an assistant or extender such as anhydrous sodium sulfate, sodium sulfate decahydrate, sodium chloride, sodium carbonate, an alkali metal phosphate such as sodium or potassium orthophosphate, sodium or potassium pyrophosphate or sodium or potassium tripolyphosphate, or an alkali metal silicate such as sodium silicate.

In addition to the compounds of formula (1), a minor proportion of one or more adjuvants may also be employed in the method of the present invention. Examples of adjuvants include emulsifiers, perfumes, colouring dyes, opacifiers, further fluorescent whitening agents, bactericides, nonionic surfactants, fabric care ingredients, especially fabric softeners, stain release or stain repellant ingredients or water-proofing agents, anti-gelling agents such as nitrites or nitrates of alkali metals, especially sodium nitrate, and corrosion inhibitors such as sodium silicate.

The amount of each of these optional adjuvants should not exceed 1%, and preferably ranges from 0.01 to 1% by weight on the treated fibre.

The method of the present invention, in addition to providing protection to the skin, also increases the useful life of a textile article treated according to the present invention. In particular, the tear resistance and/or lightfastness of the treated textile fibre material may be improved.

The present invention also provides a textile fabric produced from a fibre treated according to the method of the present invention as well as an article of clothing produced from the said fabric.

Such textile fabrics and articles of clothing produced from the said fabrics typically have an SPF rating of 20 and above whereas untreated cotton, for example, generally has an SPF rating of from 2 to 4.

The treatment method according to the present invention may also be conducted by washing the textile fibre material with a detergent containing at least one compound of formula (1), thereby imparting an excellent sun protection factor to the fibre material so washed.

The detergent treatment according to the present invention is preferably effected by washing the textile fibre material at least once with the detergent composition at a temperature ranging from 10 to 100° C., especially from 15 to 60° C.

The detergent composition used preferably comprises:
i) 5–90%, preferably 5–70% of an anionic surfactant and/or a nonionic surfactant;
ii) 5–70%, preferably 5–40% of a builder;
iii) 0–30%, preferably 1–12% of a peroxide;
iv) 0–10%, preferably 1–6% of a peroxide activator and/or 0–1%, preferably 0.1–0.3% of a bleaching catalyst;
v) 0.005–2%, preferably 0.01–1% of at least one compound of formula (1); and
vi) 0.005–10%, preferably 0.1–5% of of one or more auxiliaries, each by weight, based on the total weight of the detergent.

The said detergent compositions are also new and, as such form a further aspect of the present invention.

The detergent may be formulated as a solid, as an aqueous liquid comprising 5–50, preferably 10–35% water or as a non-aqueous liquid detergent, containing not more than 5, preferably 0–1 wt. % of water, and based on a suspension of a builder in a non-ionic surfactant, as described, e.g., in GB-A-2158454.

The anionic surfactant component may be, e.g., a sulphate, sulphonate or carboxylate surfactant, or a mixture of these.

Preferred sulphates are alkyl sulphates having 12–22 carbon atoms in the alkyl radical, optionally in combination with alkyl ethoxy sulphates having 10–20 carbon atoms in the alkyl radical.

Preferred sulphonates include alkyl benzene sulphonates having 9–15 carbon atoms in the alkyl radical.

In each case, the cation is preferably an alkali metal, especially sodium.

Preferred carboxylates are alkali metal sarcosinates of formula R—CO(R$^1$)CH$_2$COOM$^1$ in which R is alkyl or alkenyl having 9–17 carbon atoms in the alkyl or alkenyl radical, R$^1$ is C$_1$–C$_4$ alkyl and M$^1$ is alkali metal.

The nonionic surfactant component may be, e.g., a condensate of ethylene oxide with a C$_9$–C$_{15}$ primary alcohol having 3–8 moles of ethylene oxide per mole.

The builder component may be an alkali metal phosphate, especially a tripolyphosphate; a carbonate or bicarbonate, especially the sodium salts thereof; a silicate or disilicate; an aluminosilicate; a polycarboxylate; a polycarboxylic acid; an organic phosphonate; or an aminoalkylene poly (alkylene phosphonate); or a mixture of these.

Preferred silicates are crystalline layered sodium silicates of the formula NaHSi$_m$O$_{2m+1}$·pH$_2$O or Na$_2$Si$_m$O$_{2m+1}$·pH$_2$O in which m is a number from 1.9 to 4 and p is 0 to 20.

Preferred aluminosilicates are the commercially-available synthetic materials designated as Zeolites A, B, X, and HS, or mixtures of these. Zeolite A is preferred.

Preferred polycarboxylates include hydroxypolycarboxylates, in particular citrates, polyacrylates and their copolymers with maleic anhydride.

Preferred polycarboxylic acids include nitrilotriacetic acid and ethylene diamine tetra-acetic acid.

Preferred organic phosphonates or aminoalkylene poly (alkylene phosphonates) are alkali metal ethane 1-hydroxy diphosphonates, nitrilo trimethylene phosphonates, ethylene diamine tetra methylene phosphonates and diethylene triamine penta methylene phosphonates.

Any peroxide component may be any organic or inorganic peroxide compound, described in the literature or available on the market, which bleaches textiles at conventional washing temperatures, e.g. temperatures in the range of from 5° C. to 90° C. In particular, the organic peroxides are, for example, monoperoxides or polyperoxides having alkyl chains of at least 3, preferably 6 to 20, carbon atoms; in particular diperoxydicarboxylates having 6 to 12 C. atoms, such as diperoxyperazelates, diperoxypersebacates, diperoxyphthalates and/or diperoxydodecanedioates, especially their corresponding free acids, are of interest. It is preferred, however, to employ very active inorganic peroxides, such as persulphate, perborate and/or percarbonate. It is, of course, also possible to employ mixtures of organic and/or inorganic peroxides. The peroxides, especially the inorganic peroxides, are preferably activated by the inclusion of an activator such as tetraacetyl ethylenediamine or nonoyloxybenzene sulfonate. Bleaching catalysts which may be added include, e.g., enzymatic peroxide precursors and/or metal complexes. Preferred metal complexes are manganese or iron complexes such as manganese or iron phthalocyanines or the complexes described in EP-A-0509787.

The detergents used will usually contain one or more auxiliaries such as soil suspending agents, for example sodium carboxymethylcellulose; salts for adjusting the pH, for example alkali or alkaline earth metal silicates; foam regulators, for example soap; salts for adjusting the spray drying and granulating properties, for example sodium sulphate; perfumes; and also, if appropriate, antistatic and softening agents; such as smectite clays; enzymes, such as amylases and proteases; photobleaching agents; pigments; and/or shading agents. These constituents should, of course, be stable to any bleaching system employed.

Compounds of the formula (I) have also been found to be useful for the fluorescent whitening of textile materials, in which connection polyamides, wool and cotton should be singled out particularly, and of paper.

The asymmetric compounds of formula (1) offer several advantages with respect to their symmetric analogues: since more substituents are present in the molecule, the applicational properties of the corresponding symmetric analogues can be combined, or even improved; the asymmetric compounds of formula (1) dissolve in water more rapidly and to a greater extent than the corresponding symmetric analogues; and, since the colour shade and affinity are dependent on the substituent type, the fact that asymmetric compounds of formula (1) contain three different substituents gives more scope for modifying each of these important properties.

The following Examples further illustrate the present invention.

EXAMPLE 1

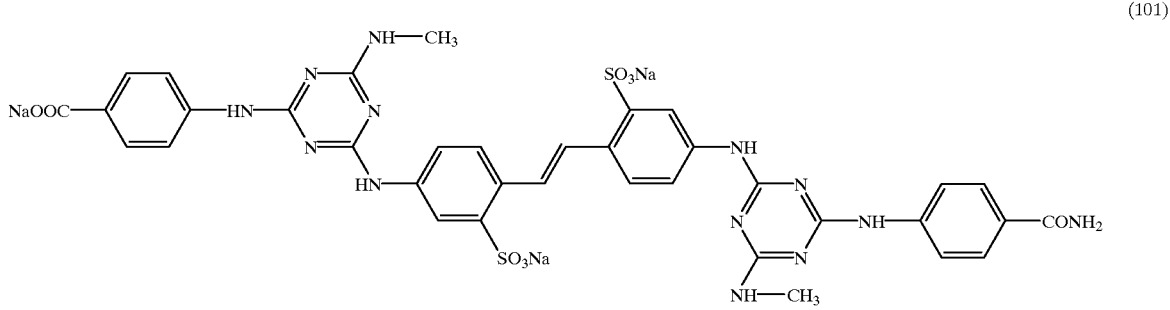

(101)

A) 8 g (20 mmol) of 4-amino-4'-nitro-2,2'-stilbenedisulfonic acid are dissolved in 90 ml of water and 20 ml of 1M aqueous soda solution at 0° C. to form solution A.

B) 3.7 g (20 mmol) of cyanuric chloride are dissolved in 20 ml of acetone and poured on to 20 ml of ice-water. To this mixture is then added, at 0° C. over 15 minutes, solution A. The pH of the mixture so obtained is then adjusted to 7 by the addition of 10 ml of 1M aqueous soda solution.

C) 2.88 g (21 mmol) of 4-aminobenzoic acid are dissolved in 10 ml of water and 10.5 ml of 1M of aqueous soda solution. This solution is then added to the mixture obtained in step B) at 55° C. while maintaining the pH value of the reaction at 8–9 by the addition of 10 ml of 1M aqueous soda solution. After 2 hours, the 4-aminobenzoic acid has fully reacted.

D) The reaction mixture from step C) is treated with 1.97 g (25 mmol) of 40% methylamine solution in water and the mixture so obtained is boiled and, after the addition of 10 ml of 1M aqueous soda solution, the reaction mixture is further heated at 55° C. for 2 hours. The intermediate product so obtained is isolated by precipitation with isopropanol to give a brick-red powder having the formula:

described in step B); with 4-aminobenzamide as described in step C), but replacing the 4-aminobenzoic acid used therein with 4-aminobenzamide; and with methylamine, as described in step D). The product so obtained is isolated by salting-out and washing with a little water. In this way, there is obtained the compound of formula (101).

Elemental analysis of the compound having the formula (101) and having the empirical formula $C_{36}H_{30}N_{13}O_9S_2Na_3 \cdot 7H_2O$ gives:

Req. % C 41.26; H 4.23; N 17.38; S 6.11; $H_2O$ 12.
Found % C 41.34; H 4.32; N 17.18; S 5.91; $H_2O$ 11.1.

EXAMPLE 2

19.3 g (100 mmol) of cyanuric chloride are dissolved in an acetone-water mixture and this solution is reacted with 18.42 g (50 mmol) of 2,2-diaminostilbene 4,4'-disulfonic acid at pH 5–5.5. 9.7 g (56 mmol) of sulfanilamide and 7.84 g (56 mmol) of 4-aminomethylbenzamide are added and the reaction temperature is raised to 55° C. The pH of the mixture is then adjusted to 8 by the addition of 1M aqueous soda solution and the mixture is stirred for 3 hours at this temperature and pH. Examination of the reaction product by HPLC showed that it consists of 3 products. The reaction product is treated with 15 g (220 mmol) of 40% aqueous methylamine solution, then 50 ml of 1M aqueous soda solution are added and the mixture is heated under reflux conditions for 3 hours until the reaction is complete. The reaction mixture so obtained is concentrated to 100 ml and

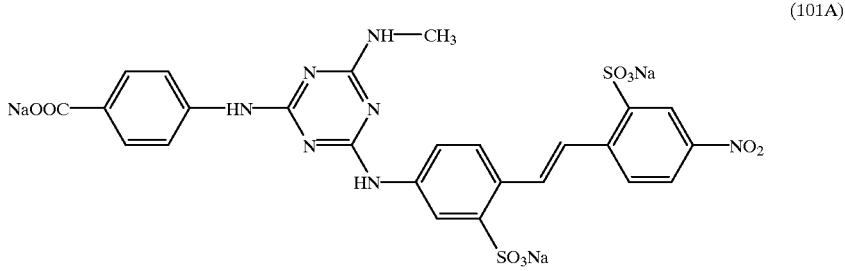

(101A)

In order to reduce the nitro group in the compound of formula (101A) to the corresponding amino group, 23 g (max. 20 mmol) of moist compound of formula (101A) are reacted with 9 g (150 mmol) of acetic acid and 21 g (376 mmol) of iron. The amino compound so obtained is then reacted sequentially with further cyanuric chloride as is added, with stirring, to a hydrochloric acid-acetone solution. A mixture of free acids is obtained which is filtered with suction and washed with acetone. The filter-cake is dispersed in ethanol-water and the pH is adjusted to 8.5. The mixture is then evaporated to to dryness. After drying, there are obtained 53 g (88% theory) of a mixed product (102)

which, according to HPLC analysis, has the following composition:

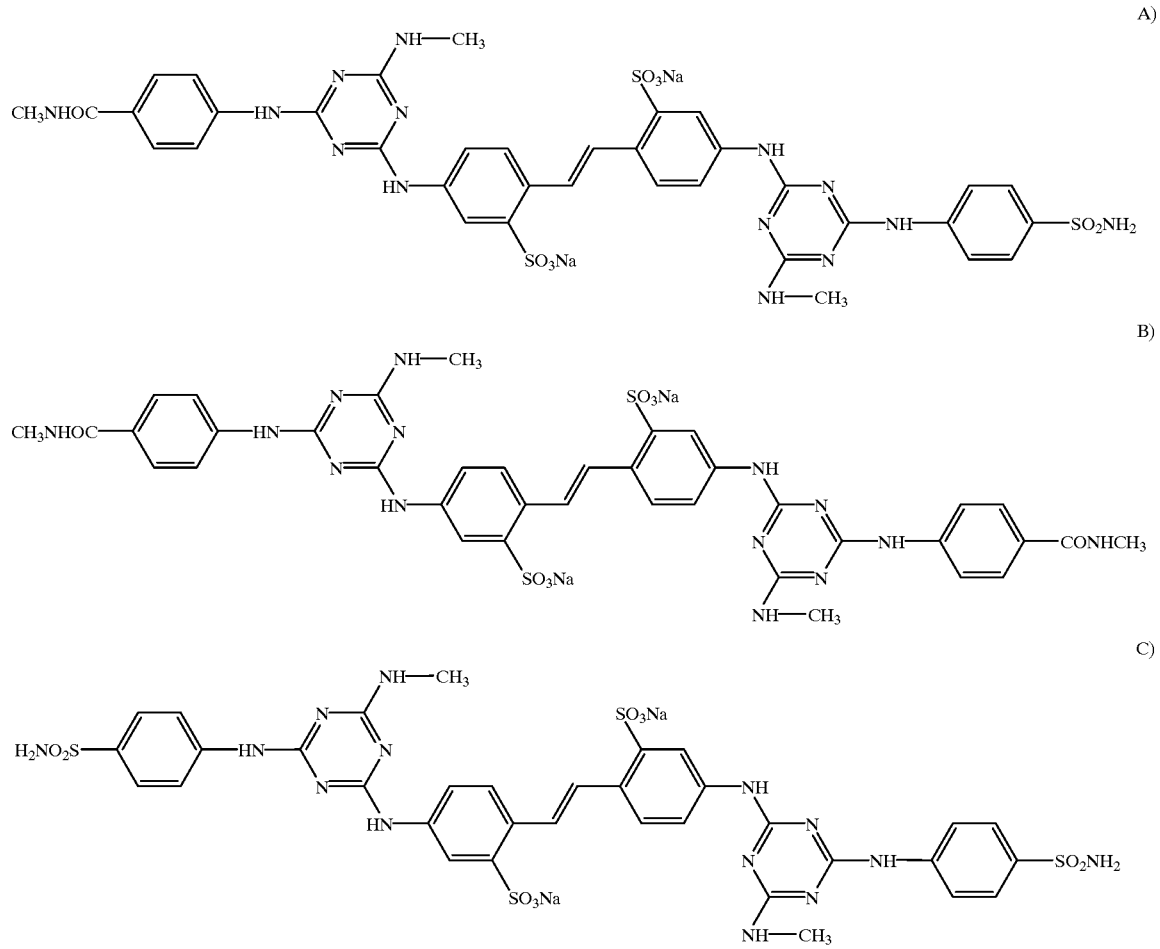

The respective % proportions of A:B:C, according to HPLC, are 50:25:25. Logically, the elemental analysis corresponds to the formula A).

Elemental analysis of the mixture (102) of compound having the respective formula A), B) or C) and having the empirical formula $C_{36}H_{34}N_{14}O_9S_3Na_2 \cdot 1NaCl \cdot 11H_2O$ gives:

Req. % C 36.14; H 4.64; N 16.2; S 7.97; Cl 2.93
Found % C 35.93; H 4.77; N 16.12; S 7.99; Cl 2.90.

EXAMPLE 3

The procedure described in Example 2 is repeated except that the sulfanilamide used therein is replaced by the equivalent amount of aniline.

There is obtained a mixed product (103) which, according to HPLC analysis, has the following composition:

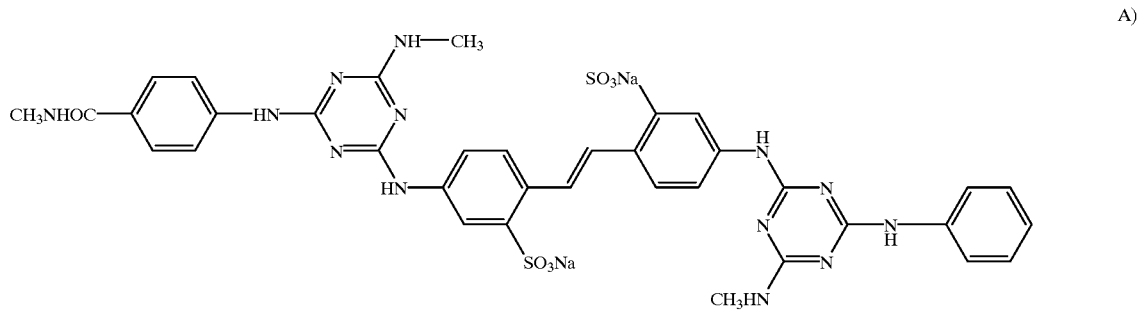

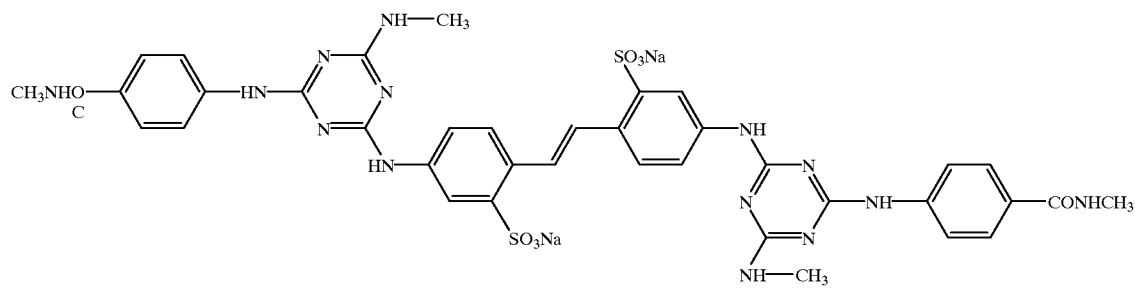

B)

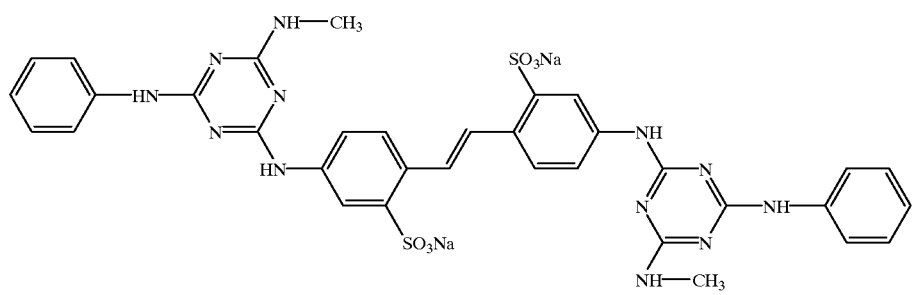

C)

The respective % proportions of A:B:C, according to HPLC, are 50:25:25. Logically, the elemental analysis corresponds to the formula A).

Elemental analysis of the mixture (103) of compound having the respective formula A), B) or C) and having the empirical formula $C_{36}H_{33}N_{13}O_7S_2Na_2 \cdot 10H_2O$ gives:

Req. % C 41.62; H 5.10; N 17.49; S 5.88.
Found % C 41.62; H 5.14; N 17.52; S 6.17.

EXAMPLE 4 with 8 g of 4-amino-4'-nitrostilbene-2,2'disulphonic acid followed by 12 g of 40% aqueous methylamine solution. Reduction of the resulting nitro compound with 21 g of iron powder and 9 g of glacial acetic acid in 150 ml of water yields 8.2 g of the intermediate amine of formula (104)

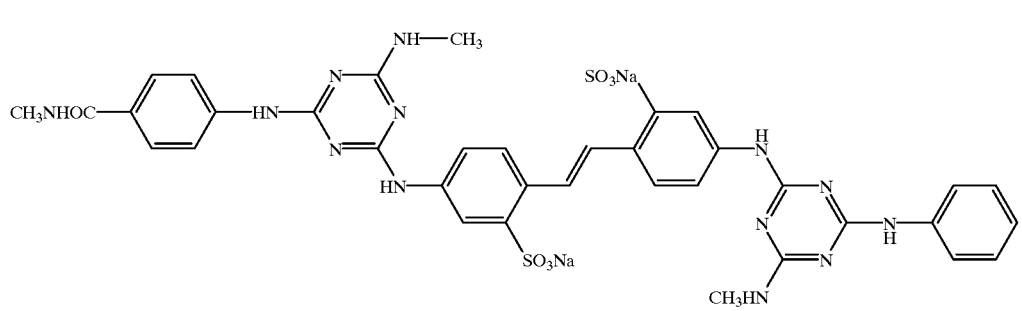

According to the method described in Example 1, 3.8 g of cyanuric chloride are reacted in an acetone/water mixture

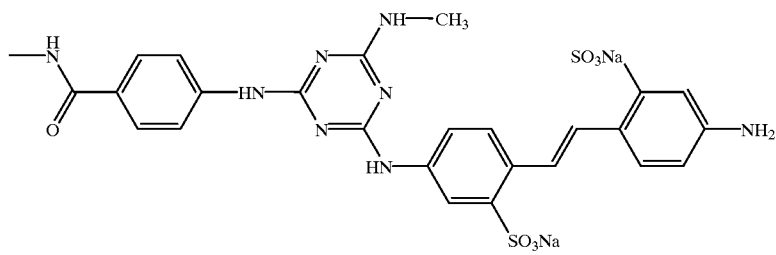

(104A)

Successive reaction of this compound with cyanuric chloride, aniline and methylamine in acetone/water according to the procedure described in Example 1D yields compound (104). having the following elemental analysis: $C_{36}H_{33}N_{13}O_7S_2Na_2 \cdot 10H_2O$ Req. % C 41.62; H 5.10; N 17.49; S 5.88.

Found % C 41.62; H 5.14; N 17.52; S 6.17.

EXAMPLE 5 procedure described in Example 2 is repeated except that the 4-aminobenzamide used therein is replaced by the equivalent amount of 4-aminoacetophenone, the sulfanilamide by 4-aminobenzamide and the methylamine by 2-methoxyethylamine. There is obtained a mixed product (105) which, according to HPLC analysis, has the following composition:

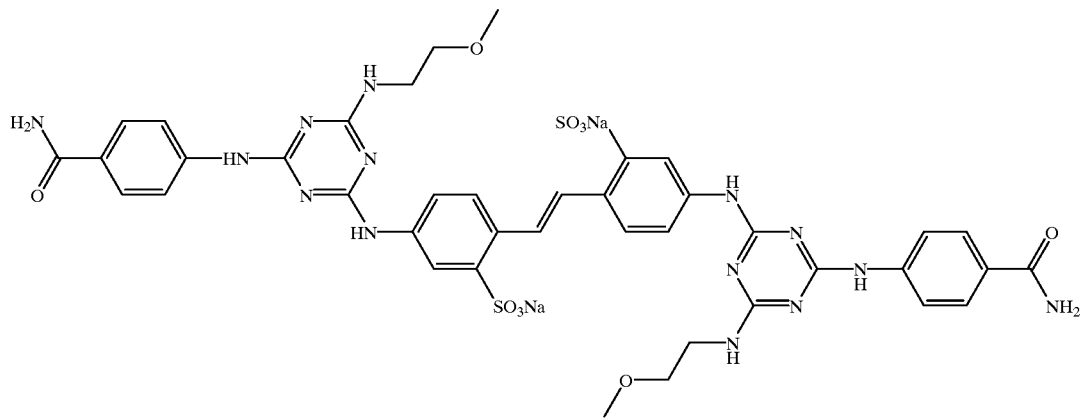

A)

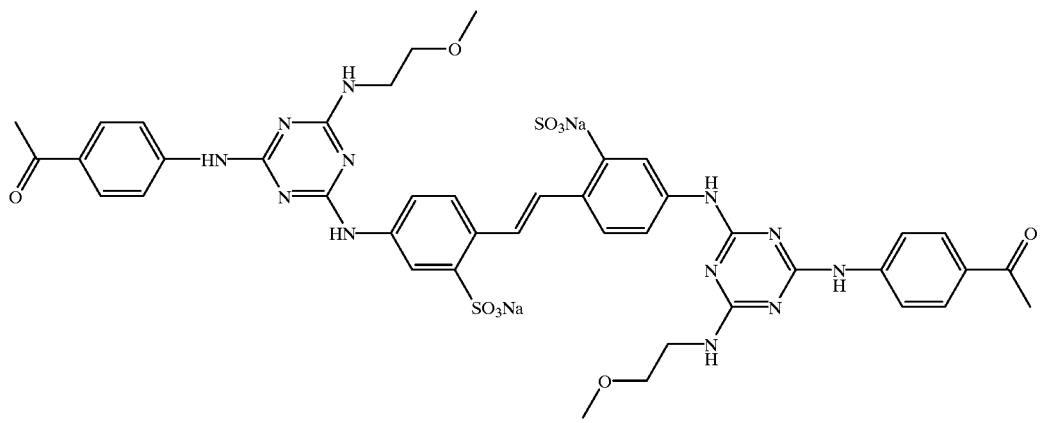

B)

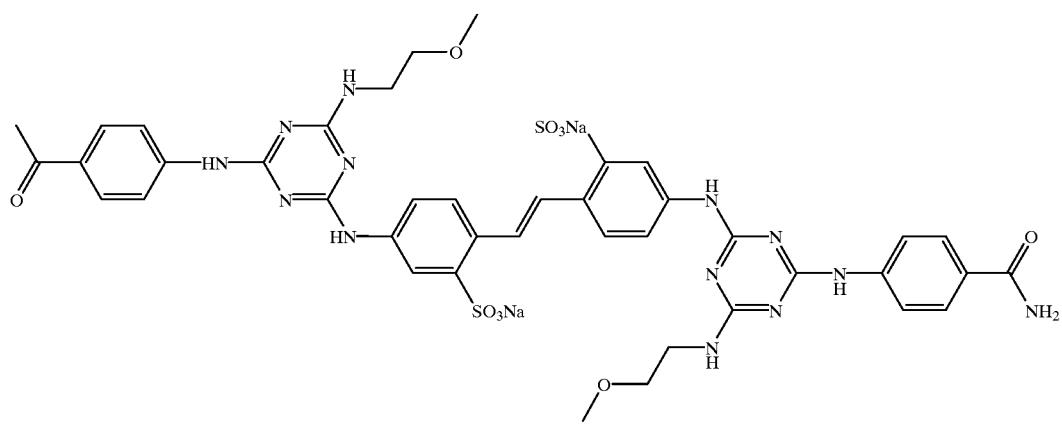
C)

The respective % proportions of A:B:C, according to HPLC, are 25:25:50. Logically, the elemental analysis corresponds to the formula A).

Elemental analysis of the mixture (105) of compound having the respective formula A), B) or C) and having the empirical formula $C_{41}H_{14}N_{13}Na_2O_{10}S_2$, 0.4 NaCl and 9.15H$_2$O gives:

Req. % C 41.95; H 5.09; N; 15.51; S; 5.46; Cl 1.21; Water 14.03

Found % C 42.0; H 5.1; N 15.6; S 5.5; Cl 1.1; Water 14.05

By following the procedure described in Example 1, but substituting the 4-aminobenzoic acid methylamine and 4-aminobenzamide by equimolar quantities of the appropriate amines, the compounds of formula (3) in the following Table I may also be obtained.

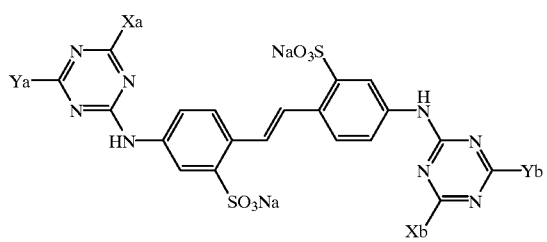

(3)

TABLE 1

| Compound | Xa | Xb | Ya | Yb |
|---|---|---|---|---|
| (106) | CH$_3$NH | (HOCH$_2$CH$_2$)$_2$N | phenyl-NH | 4-acetyl-phenyl-NH |
| (107) | C$_2$H$_5$NH | C$_2$H$_5$NH | 4-(acetamido)-phenyl-NH | phenyl-NH |

TABLE 1-continued

| Compound | Xa | Xb | Ya | Yb |
|---|---|---|---|---|
| (108) | n-C$_3$H$_7$NH | CH$_3$NH | (H$_3$C)$_2$N-C(=O)-NH-C$_6$H$_4$-NH- | C$_6$H$_5$-NH- |
| (109) | HO$_2$CCH$_2$NH | CH$_3$NH | C$_6$H$_5$-NH- | CH$_3$C(=O)-C$_6$H$_4$-NH- |
| (110) | (CH$_3$)$_2$N | C$_2$H$_5$NH | C$_6$H$_5$-NH- | (CH$_3$)$_2$NSO$_2$-C$_6$H$_4$-NH- |
| (111) | CH$_3$NH | morpholino | CH$_3$C(=O)-C$_6$H$_4$-NH- | NC-C$_6$H$_4$-NH- |
| (112) | (CH$_3$)$_2$NC$_2$H$_4$NH | CH$_3$NH | C$_6$H$_5$-NH- | CH$_3$NHC(=O)-C$_6$H$_4$-NH- |

By repeating the procedure described in Example 2, utilising the corresponding amines, mixtures of the above compounds (106)–(112) together with the corresponding symmetric derivatives may be obtained.

EXAMPLE 6

A standard (ECE) washing powder is made up from the following components in the indicated proportions (weight %):

| | |
|---|---|
| 8.0% | Sodium (C$_{11.5}$)alkylbenzene sulfonate |
| 2.9% | Tallow alcohol-tetradecane-ethylene glycol ether (14 mols EO) |
| 3.5% | Sodium soap |
| 43.8% | Sodium tripolyphosphate |
| 7.5% | Sodium silicate |
| 1.9% | Magnesium silicate |
| 1.2% | Carboxymethyl cellulose |
| 0.2% | EDTA |
| 21.2% | Sodium sulfate |
| 0 or 0.2% | compound (103) and Water to 100%. |

5 g. of bleached cotton fabric is washed in a wash liquor containing 4 g/l of the above washing powder and water (liquor ratio 1:20) at 40° C. in a Linitest apparatus over 15 minutes and then rinsed, spin-dried and ironed at 160° C. This washing procedure is repeated three times and 10 times respectively.

After the third and tenth washes, the whiteness of the washed samples is measured with a DCI/SF 500 spectrophotometer according to the Ganz method. The Ganz method is described in detail in the Ciba-Geigy Review, 1973/1, and also in the article "Whiteness Measurement", ISCC Conference on Fluorescence and the Colorimetry of Fluorescent Materials, Williamsburg, February 1972, published in the Journal of Color and Appearance, 1, No.5 (1972). The Sun Protection Factor (SPF) is also determined by measurement of the UV light transmitted through the swatch, using a double grating spectrophotometer fitted with an Ulbricht bowl. Calculation of SPF is conducted as described by B. L. Diffey and J. Robson in J. Soc. Cosm. Chem. 40 (1989), pp. 130–131.

The results obtained are set out in the following Table 2:

TABLE 2

| Example | Test Compound | SPF 10 washes | W 3 washes | W 10 washes |
|---|---|---|---|---|
| — | none (control) | 3 | 72 | 75 |
| 4 | compound (103) | 20 | 218 | 234 |

Compared with the control experiment, the SPF values obtained according to the invention are 6–7 times higher.

EXAMPLE 7

An aqueous bleach liquor having a liquor ratio of 1:40 (deionised water) is formulated containing 0.025, 0.05, 0.1 or 0.2 weight % of a test fluorescent whitening agent; 5 ml/l of a 10% solution of Ultravon EL; 20 ml/l of a 3% solution of of NaOH; 5 ml/l of a 10% solution of Tinoclarit GS; and 3 ml/l of a 35% solution of hydrogen peroxide.

A bleached cotton sample is immersed in the bleach liquor and the liquor is heated to 85° C. over 30 minutes, held at this temperature for 60 minutes and then cooled from 85° C. to 40° C. over 20 minutes. The degree of exhaustion of the test fluorescent whitening agent on to the cotton substrate is then determined by measuring the Ganz whiteness of each treated cotton sample. The results are set out in the following Table 3.

TABLE 3

| | | Ganz Whiteness/concentration FWA | | | |
|---|---|---|---|---|---|
| Example | Test FWA | 0.025% | 0.05% | 0.1% | 0.2% |
| 5 | compound 102 | 208 | 223 | 239 | 242 |

What is claimed is:

1. An asymmetric UV absorbing compound having the formula:

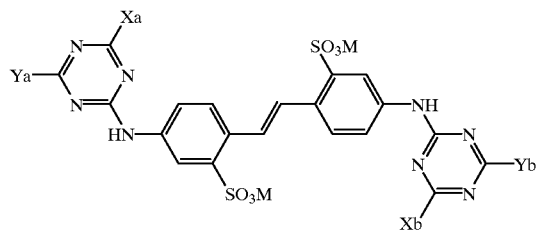

in which M is hydrogen, an alkali metal atom, calcium, magnesium, ammonium or a cation formed from an amine;

Xa and Xb are the same or different and each is $NH_2$; $NH(C_1-C_4 alkyl)$; $N(C_1-C_4 alkyl)_2$; $NH(C_2-C_4 alkoxyalkyl)$; $N(CH_2CH_2OH)_2$; a group $NH-Z-NR_1R_2$ in which Z is $C_2-C_{14}$alkylene or optionally substituted arylene, and $R_1$ and $R_2$ are the same or different and each is $C_1-C_{12}$alkyl or $R_1$ and $R_2$, together with the nitrogen atom to which they are each attached, form a morpholino, piperidino or piperazino ring; or is an aminoacid residue; $C_1-C_4$alkoxy; or hydroxy-substituted-$C_2-C_4$alkoxy; and Ya and Yb are the same or different and each is a substituted amino group having both UVA and UVB-absorbing properties, and provided that one of Xa and Xb is different from the other and/or one of Ya and Yb is different from the other, whereby Ya and Yb each is a group having the formula:

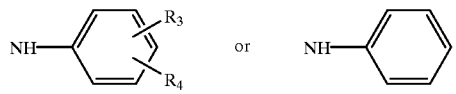

in which $R_3$ is CN; $SO_2R_5$ in which $R_5$ is $C_1-C_{12}$alkyl, $C_1-C_{12}$alkoxy, $NH_2$, $NH(C_1-C_4 alkyl)$, $N(C_1-C_4 alkyl)_2$, $N(CH_2CH_2OH)_2$, $C_1-C_4$alkoxy-substituted-$C_2-C_4$alkoxy or hydroxy-substituted-$C_2-C_4$alkoxy; $COR_5$ which $R_5$ has its previous definition; COOM in which M has its previous definition or $NHCOR_5$ in which $R_5$ has its previous definition and in which $R_4$ has the same definition as $R_3$ or is H, OH, $C_1-C_4$alkyl or $C_1-C_4$alkoxy, with the proviso that when $R_3$ is COOM, Ya and Yb are different.

2. A compound according to claim 1 in which M is hydrogen, sodium, potassium, calcium, magnesium, ammonium, mono-, di-, tri- or tetra-$C_1-C_4$alkylammonium, mono-, di-, tri- or tetra-$C_1-C_4$hydroxyalkylammonium, or ammonium that is di- or tri-substituted with with a mixture of $C_1-C_4$alkyl and $C_1-C_4$hydroxyalkyl groups.

3. A compound according to claim 2 in which each M is sodium.

4. A compound according to claim 1 in which one or more of Xa, Xb and $R_5$ are $NH(C_1-C_4 alkyl)$, [NH$(C_2-C_4 alkoxyalkyl),$] or one or more of Xa, Xb and $R_5$ are $N(C_1-C_4 alkyl)_2$ groups or one or both of Xa and Xb are $NH(C_1-C_4 alkoxyalkyl)$.

5. A compound according to claim 1 in which one or both of Xa and Xb is a group $NH-Z-NR_1R_2$, in which the $C_2-C_{14}$alkylene group Z is a 1,3-propylene group.

6. A compound according to claim 1 in which Xa and/or Xb is an aminoacid residue having the formula $-NH-CH(CO_2H)-R_6$ in which $R_6$ is hydrogen or a group having the formula —CHR$_7$R$_8$ in which R$_7$ and R$_8$, independently, are hydrogen or C$_1$–C$_4$alkyl optionally substituted by one or two substituents selected from the group consisting of hydroxy, thio, methylthio, amino, carboxy, sulfo, phenyl, 4-hydroxyphenyl, 3,5-diiodo-4-hydroxyphenyl, β-indolyl, β-imidazolyl and NH=C(NH$_2$)NH—.

7. A compound according to claim 6 in which the aminoacid from which the aminoacid residues Xa and/or Xb are derived is glycine, alanine, sarcosine, serine, cysteine, phenylalanine, tyrosine (4-hydroxyphenylalanine), diiodotyrosine, tryptophan (β-indolylalanine), histidine ((β-imidazolylalanine), α-aminobutyric acid, methionine, valine (α-aminoisovaleric acid), norvaline, leucine (α-aminoisocaproic acid), isoleucine (α-amino-β-methylvaleric acid), norleucine (α-amino-n-caproic acid), arginine, ornithine (α,δ-diaminovaleric acid), lysine (α,ε-diaminocaproic acid), aspartic acid (aminosuccinic acid), glutamic acid (α-aminoglutaric acid), threonine, hydroxyglutamic acid and taurine, or a mixture or optical isomer thereof.

8. A compound according to claim 7 in which the aminoacid from which the aminoacid residues Xa and/or Xb is derived is sarcosine, taurine, glutamic acid or aspartic acid.

9. A compound according to claim 1 in which Xa and/or Xb, R$_4$ or R$_5$ is a methoxy residue or a 2-hydroxy-ethoxy group.

10. A compound according to claim 1 in which R$_4$ is hydrogen or a methyl group.

11. A compound according to claim 1 in which, in the groups Ya and Yb of formula (2), the substituents R$_3$ and R$_4$ are in the 2- and 4-positions relative to the NH substituent.

12. A compound of formula (1) according to claim 1 which is obtained in the form of a mixture with the analogous symmetrical compounds in which the groups Xa and Xb and the groups Ya and Yb are the same by reacting, in one pot, the respective stoichiometric amounts of cyanuric chloride, an aminostilbene-sulfonic acid, an amino compound capable of introducing a group Xa and Xb, in which Xa and Xb are as defined in claim 1, and a compound capable of introducing a group Ya and Yb, in which Ya and Yb are as defined in claim 1.

13. A compound according to claim 1 in which Xa and Xb are the same and Ya and Yb are different.

* * * * *